United States Patent [19]

Cook

[11] Patent Number: 4,536,181

[45] Date of Patent: Aug. 20, 1985

[54] SANITARY NAPKIN WITH IMPROVED PROTECTION

[76] Inventor: Linda E. Cook, 4314 Lasalle Ave., Baltimore, Md. 21206

[21] Appl. No.: 596,318

[22] Filed: Apr. 3, 1984

[51] Int. Cl.³ .............................................. A61F 13/16
[52] U.S. Cl. ..................................................... 604/387
[58] Field of Search .............. 604/387, 389, 390, 391, 604/397, 398, 399, 400, 401, 402

[56] References Cited

U.S. PATENT DOCUMENTS

| | | | |
|---|---|---|---|
| 2,522,008 | 9/1950 | Wohlman | 604/397 |
| 2,840,078 | 6/1958 | Smith | 604/397 |
| 3,897,783 | 8/1975 | Ginocchio | 604/390 |
| 3,973,567 | 8/1976 | Srinioasan | 604/390 |

FOREIGN PATENT DOCUMENTS 862763  3/1961  United Kingdom ................ 604/399

Primary Examiner—John D. Yasko
Assistant Examiner—Christa K. Scott
Attorney, Agent, or Firm—Leonard Bloom

[57] ABSTRACT

A back panty shield for a conventional sanitary napkin for feminine usage has a substantially unitary member having a forward portion that, in plan outline, flares outwardly to an enlarged rearward portion. The shield may be readily attached to the napkin by means of a transverse adhesive strip, and the disposition of the napkin relative to the shield may be adjusted to accommodate various wearers. Means are provided to removably secure the shield (as well as the napkin) to the wearer's undergarment, if desired. With this arrangement, additional protection is provided for the wearer, particularly during sleeping hours. In an alternate embodiment, the back panty shield is formed integrally with the sanitary napkin and is made relatively thin.

8 Claims, 11 Drawing Figures

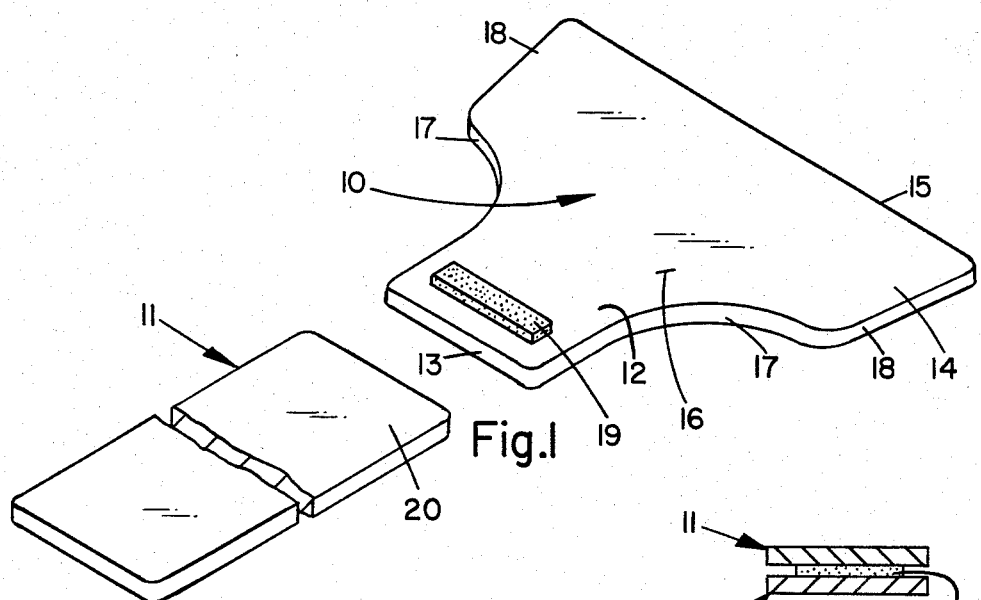
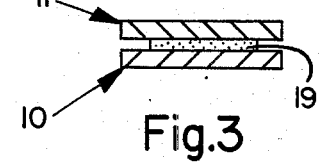
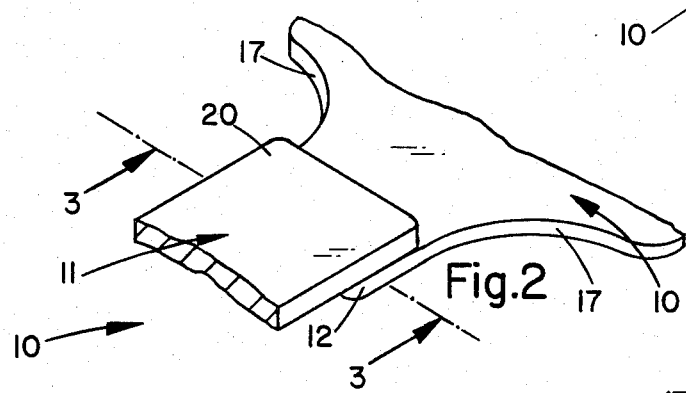
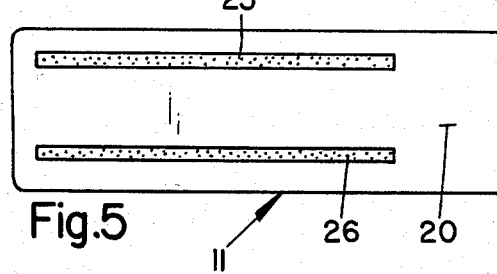
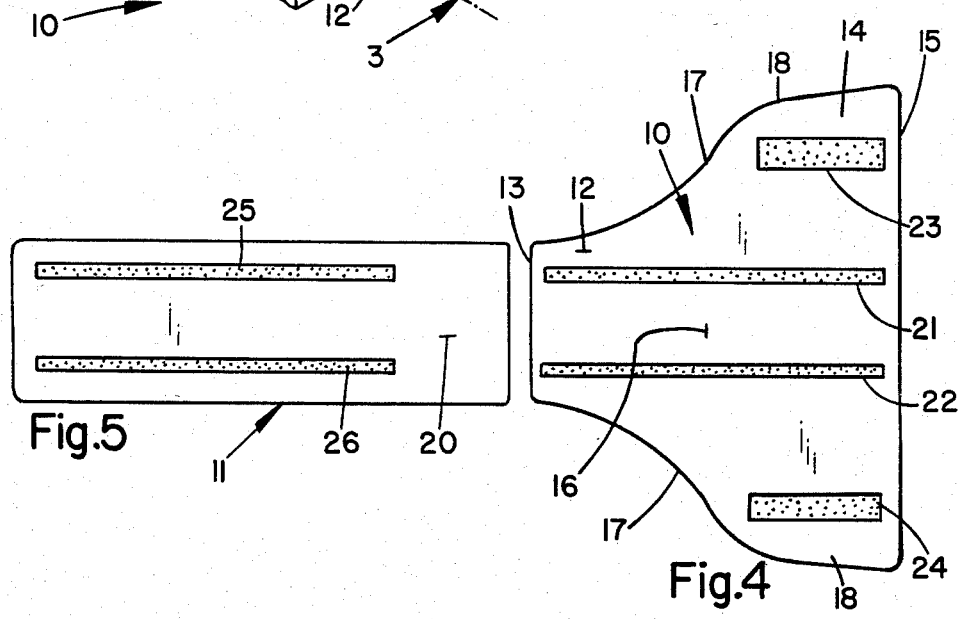

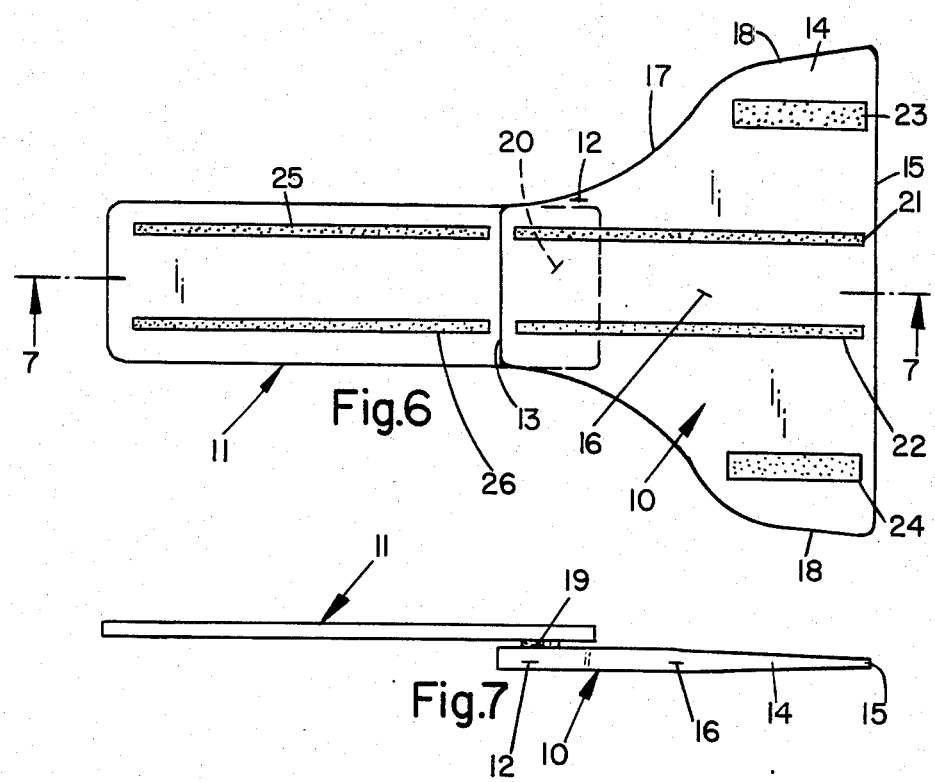
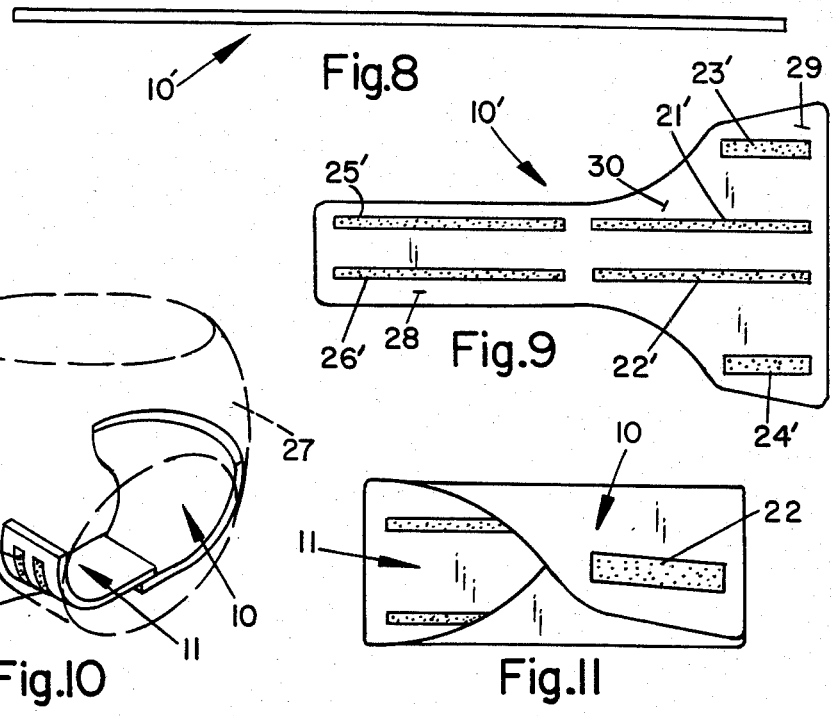

SANITARY NAPKIN WITH IMPROVED PROTECTION

FIELD OF THE INVENTION

The present invention relates to an improved sanitary napkin for feminine usage, and more particularly, to a removable back panty shield which forms an optional continuation of the sanitary napkin and provides additional protection for the wearer such as during sleeping hours.

BACKGROUND OF THE INVENTION

While the conventional sanitary napkin is adequate for most purposes during daily usage, it does not provide complete protection for the wearer at all times. For example, when the wearer is sleeping on her back, the conventional napkin does not provide sufficient protection to absorb normal menstrual flow. The flow tends to trickle down on the backside of the undergarments or nightgown, and the mattress on the bed often becomes soiled. To prevent soilage, some women resort to the use of two napkins or a large towel between their body and the mattress.

In addition, when the wearer is sitting in substantially the same position for an extended duration, such as during a trip or while working on a job, the sanitary napkin may tend to "ride up", that is, shift forwardly and upwardly. As a result, the coverage is insufficient or incomplete, the clothing may become soiled, and these situations make the wearer uncomfortable and may cause embarrassment.

In an apparent effort to correct this deficiency, the prior art has resorted to a variety of enlarged sanitary napkins, diapers, or complicated belts, which may be sufficient for hospital or medical usage, but which are inadequate for normal daily usage.

SUMMARY OF THE INVENTION

Accordingly, it is an object of the present invention to provide an improved sanitary napkin which alleviates the deficiencies and disadvantages of the prior art.

It is a further object of the present invention to provide a removable back panty shield for substantially any type of conventional sanitary napkin for optional usage, thereby providing additional protection such as during sleeping hours or while sitting for an extended duration.

It is yet another object of the present invention to provide a disposable attachment that may be manufactured easily and economically for widespread consumer marketing through normal channels of distribution.

It is a further object to provide a back panty shield that may be used for either bikini briefs or for regular waist-line undergarments.

It is a still further object to provide a back panty shield that is sufficiently thick at the bottom (or forward portion) but which "feathers" at the top, so that it is relatively thin, unobtrusive, and may be worn with tight-fitting garments.

In accordance with the teachings of the present invention, there is provided a preferred embodiment of a removable back panty shield for a sanitary napkin. The shield comprises a disposable unitary member having a forward portion and a rearward portion, each of which has a respective end edge. The shield further has a main body portion intermediate its forward and rearward portions. The rearward portion has a substantially greater transverse width than the width of the forward portion, such that in plan outline the shield flares outwardly substantially continuously from its forward portion to its rearward portion. The forward portion of the shield has means, such as a transverse adhesive strip, to facilitate a removable attachment to the sanitary napkin. With this arrangement, the shield forms an optional continuation of the sanitary napkin and provides additional protection for the wearer such as during sleeping hours. Preferably, the shield carries further means for removable attachment to an undergarment of the wearer.

These and other objects of the present invention will become apparent from a reading of the following specification taken in conjunction with the enclosed drawings.

BRIEF DESCRIPTION OF THE DRAWINGS

FIG. 1 is a perspective view of the back panty shield of the present invention in exploded relation to the conventional sanitary napkin.

FIG. 2 corresponds substantially to a portion of FIG. 1, but shows the shield removably secured to the napkin.

FIG. 3 is a section view, taken along the lines 3—3 of FIG. 2, and showing a preferred attachment means.

FIG. 4 is a plan outline of the underside of the shield, showing the plurality of adhesive strips for removable attachment to an undergarment of the wearer.

FIG. 5 is a plan outline of the underside of the sanitary napkin, showing the pair of relatively-thin adhesive strips carried thereon.

FIG. 6 shows the shield removably secured to the sanitary napkin.

FIG. 7 is a section view, taken across the lines 7—7 of FIG. 6, and showing how the thickness of the shield decreases towards its rearward portion.

FIG. 8 is a section view of an alternate embodiment, corresponding substantially to FIG. 7, but showing the back panty shield formed integrally with a relatively-thin sanitary napkin.

FIG. 9 is a plan outline of the alternate embodiment of FIG. 8, drawn to a reduced scale.

FIG. 10 is a perspective view, showing the shield and its sanitary napkin removably secured to the undergarment of the wearer.

FIG. 11 shows how the shield and its sanitary napkin may be conveniently folded up and disposed of after usage.

DESCRIPTION OF THE PREFERRED EMBODIMENT

With reference to FIGS. 1-6 of the drawings, there is illustrated a preferred embodiment of the back panty shield 10 of the present invention, comprising a disposable unitary member for removable attachment to a conventional sanitary napkin 11. The shield 10 has a forward portion 12 with an end edge 13, a rearward portion 14 with an end edge 15, and a main body portion 16 intermediate its forward and rearward portions. The rearward portion has a substantially greater transverse width than the width of the forward portion, such that in plan outline the member is substantially Vee-shaped and flares outwardly substantially continuously from its forward portion towards its rearward portion, thereby defining respective curved side edges 17, and then terminating in respective side edges 18.

A transverse adhesive strip 19 is carried on the forward portion of the shield, substantially adjacent to the end edge thereof. Preferably, the transverse adhesive strip 19 is relatively wide, such that an end portion 20 of the substantially-rectangular sanitary napkin may overlap the shield and may be removably secured thereto by means of the transverse adhesive strip as shown more clearly in FIGS. 2, 3, 6 and 7. Substantially any type of conventional sanitary napkin available on the market may be used, according to the wearer's preferences. Thus mini or maxi pads may be used, and the length of the pad or napkin may be adjusted relative to the shield to accommodate the individual user. Thus the sanitary napkin may be readily replaced and disposed of, and if desired, the shield 10 may be used repeatedly with additional sanitary napkins. Conversely, in certain instances it may only be necessary to replace the back panty shield. Eventually, the shield will also be disposed.

The underside of the disposable shield 10 has a plurality of relatively-thin substantially-parallel spaced-apart adhesive strips, preferably four in number, as at 21, 22, 23, and 24 respectively. Adhesive strips 21 and 22 form substantial continuations of the adhesive strips 25 and 26, respectively, on the underside of the conventional sanitary napkin. Adhesive strips 23 and 24, as shown more clearly in FIG. 4, are carried by the outwardly-flared rearward portion of the member. All of the adhesive strips may have a conventional protective layer or "tab" (not shown) which may be conveniently peeled off and discarded.

With this arrangement, the combination of the back panty shield 10 and the conventional sanitary napkin 11 may be removably secured to the undergarment or panty 27 of the wearer, as shown more clearly in FIG. 10. In use, the napkin 11 may first be applied to the panty; the tab (not shown) on the transverse adhesive strip 19 may be removed; the shield 10 may then be applied to the napkin and adjusted to the desired position; the panty may be pulled up; the shield may be smoothed out; and the tabs (not shown) on the adhesive strips 21-24 on the shield 10 may be removed, so that the shield may be pressed against the panty to properly stick thereto.

Thus, with this improvement, additional optional protection is provided for the wearer at all times and in particular, during sleeping hours or while sitting for an extended duration, such as on trips, to avoid embarrassing situations. The back panty shield is not bulky or complicated and will fit smoothly within the wearer's undergarment, so as not to be apparent. The shield may be manufactured easily and economically, and may be packaged attractively and promoted for widespread marketing and distribution. After use, and as shown more clearly in FIG. 11, the shield as well as the sanitary napkin may be folded up together for unobtrusive disposal.

With reference to FIG. 7, the forward portion of the back panty shield 10 preferably has substantially the same thickness as that of conventional sanitary napkin 11 to which it is removably secured. Also, the shield is formed from substantially the same material as that of the sanitary napkin. The conventional sanitary napkin is usually formed from a gauze-like material which is covered by a thin layer of cloth or synthetic material; thus the napkin is absorbent, but maintains its structural integrity. The thickness of the shield, however, preferably decreases from its forward portion to its rearward portion, that is, it is "feathered" or tapered rearwardly as shown more clearly in FIG. 7. This assures that sufficient protection will be obtained where needed, but that the shield will not be bulky and obtrusive, nor readily apparent whenever designer jeans or other tight-fitting clothing is being worn.

In a preferred embodiment, the back panty shield 10 of the present invention is approximately six inches long from its forward edge 13 to its rearward edge 15. The conventional sanitary napkin is generally rectangular in plan outline and is usually around eight to ten inches long. When overlapped in its removable attachment to the back panty shield, the overall length is approximately twelve to fourteen inches long. Also, the transverse width of the rearward edge 15 of the shield is approximately eight inches. These dimensions, of course, are illustrative only and are not intended to limit the scope of the invention.

With reference to FIGS. 8 and 9, an alternate embodiment is shown, wherein the back panty shield 10' is formed integrally with the sanitary napkin. This embodiment may be suitable with the material used on a relatively-new sanitary napkin or pad sold by Kimberly-Clark under the trademark "NEW FREEDOM". The shield 10' will have a plan outline which is substantially similar to the combination of the napkin and shield attachment as shown in FIG. 6, that is, it includes a substantially-rectangular elongated forward portion 28, an outwardly-flared rearward portion 29, and an intermediate portion 30 therebetween. The transverse width of the intermediate portion increases substantially continually from the forward portion to the rearward portion. The adhesive strips are similar to that of the preferred embodiment and are denoted at 21'-26', respectively. The shield 10' is substantially homogeneous. Additional protection is provided for the wearer, yet the shield 10' is relatively thin, hence is unobtrusive and not apparent even when a tight-fitting outer garment is worn. The shield 10' may also be folded up and discarded similarly to the embodiment of FIG. 11.

The back panty shield of the present invention is also ideal for women who have recently delivered babies, since the women will be in the hospital bed for several days and will have a relatively heavy flow subsequent to delivery. If desired, the shield may also be worn without a napkin, as for example by those suffering from colitis who need protection against inadvertent bowel movements.

Obviously, many modifications may be made without departing from the basic spirit of the present invention. Accordingly, it will be appreciated by those skilled in the art that within the scope of the appended claims, the invention may be practiced other than has been specifically described herein.

I claim:

1. A back panty shield for a sanitary napkin, comprising a disposable unitary member having a forward portion and a rearward portion, each of which has a respective end edge, the shield further having a main body portion intermediate its forward and rearward portions, the rearward portion having a substantially greater transverse width than the width of the forward portion, such that in plan outline the shield flares continuously from its forward portion to its rearward portion, means carried by the forward portion of the shield for removable attachment to the sanitary napkin, whereby the shield forms an optional continuation of the sanitary napkin and provides additional protection for the wearer such as during sleeping hours, and further means carried by the shield for removable attachment to an undergarment of the wearer.

2. The shield of claim 1, wherein the shield is made from substantially the same material as that of the sanitary napkin, wherein the forward portion of the shield has substantially the same thickness as that of the sanitary napkin, and wherein the thickness of the main body and rearward portions of the shield decreases from the forward portion to the rearward portion.

3. The shield of claim 1, wherein the means carried by the forward portion of the shield for removable attachment to the sanitary napkin comprises a transverse adhesive strip on the forward portion and disposed substantially adjacent to the end edge thereof, the sanitary napkin having an end portion which overlaps the shield and is removably secured to the transverse adhesive strip, and the transverse adhesive strip being relatively wide so that the disposition of the sanitary napkin in relation to the shield may be adjusted to accommodate various wearers.

4. The shield of claim 1, wherein the further means carried by the shield for removable attachment to an undergarment of the wearer comprises a plurality of substantially-parallel spaced-apart adhesive strips.

5. The shield of claim 4, wherein there are four adhesive strips, two on the main body portion of the shield from the forward to the rearward portions thereof, and the other two carried by the outwardly-flared rearward portion of the shield.

6. The shield of claim 5, wherein the sanitary napkin has a pair of longitudinal adhesive strips, and wherein the adhesive strips on the main body portion of the shield form substantial continuations of the longitudinal adhesive strips on the sanitary napkin.

7. A back panty shield for a sanitary napkin, comprising a disposable unitary member having a forward portion and a rearward portion, each of which has a respective end edge, the shield further having a main body portion intermediate its forward and rearward portions, the rearward portion having a substantially greater transverse width than the width of the forward portion, such that in plan outline the shield flares outwardly substantially continuously from its forward portion to its rearward portion, the forward portion of the shield having substantially the same thickness as that of the sanitary napkin, and the main body portion of the shield having a decreasing thickness from the forward portion to the rearward portion of the shield, a transverse adhesive strip carried by the forward portion of the shield substantially adjacent to the end edge thereof, the sanitary napkin having an end portion which overlaps the shield and is removably secured thereto by the transverse adhesive strip, the transverse adhesive strip being relatively wide, whereby the disposition of the sanitary napkin relative to the shield may be adjusted to accommodate various wearers, and whereby the shield forms an optional continuation of the sanitary napkin and provides additional protection for the wearer such as during sleeping hours, and a plurality of substantially-parallel spaced-apart adhesive strips carried by the shield to facilitate removable attachment to an undergarment of the wearer.

8. A combined back panty shield and sanitary napkin, comprising a unitary member whose plan outline includes a substantially-rectangular elongated forward portion, an outwardly-flared rearward portion, and an intermediate portion therebetween having a transverse width which increases substantially continually from the forward portion to the rearward portion, a first pair of relatively-thin, spaced-apart adhesive strips carried by the forward portion, a second pair of relatively-thin adhesive strips carried by the intermediate portion and rearward portion and forming a substantial continuation of the first pair of adhesive strips, a third pair of adhesive strips carried by the outwardly-flared rearward portion, whereby the member may be removably secured to the undergarment of the wearer, and whereby additional protection is provided for the wearer, the member being substantially homogeneous and further being relatively thin, whereby the shield is unobtrusive and not apparent even when a tight-fitting outer garment is worn, and whereby the member may be readily folded up for subsequent discarding by lapping the elongated forward portion over the intermediate portion and then folding the respective outwardly-flared portion of the rearward portion laterally inwardly and over the forward portion.

* * * * *